United States Patent [19]

Kepley

[11] Patent Number: 5,331,951
[45] Date of Patent: Jul. 26, 1994

[54] PHACOEMULSIFICATION PROBE DRIVE CIRCUIT

[75] Inventor: Kevin P. Kepley, Dellwood, Mo.

[73] Assignee: American Cyanamid Company, Stamford, Conn.

[21] Appl. No.: 940,980

[22] Filed: Sep. 4, 1992

[51] Int. Cl.$^5$ .............................................. A61B 8/10
[52] U.S. Cl. ..................................... 601/4; 310/316; 604/20
[58] Field of Search ...................... 606/107, 127, 128; 604/22; 128/24 AA; 310/316, 317; 323/351, 285, 287, 282; 330/297; 363/21

[56] References Cited

U.S. PATENT DOCUMENTS

| 4,378,530 | 3/1983 | Garde | 330/297 |
| 4,587,958 | 5/1986 | Noguchi et al. | 128/24 A |
| 4,739,345 | 12/1988 | Lehmer | 128/303.13 |
| 4,827,911 | 5/1989 | Broadwin | 128/24 AA |
| 5,042,460 | 8/1991 | Sakurai et al. | 128/24 AA |
| 5,121,023 | 6/1992 | Abel | 310/316 |
| 5,151,085 | 9/1992 | Sakurai et al. | 604/22 |
| 5,220,272 | 6/1993 | Nelson | 323/282 |

Primary Examiner—Lee S. Cohen
Assistant Examiner—Brian M. Green
Attorney, Agent, or Firm—Polster, Lieder, Woodruff & Lucchesi

[57] ABSTRACT

A drive for a phacoemulsification probe includes a drive circuit for supplying electrical power to the probe, circuitry for sensing the electrical power supplied by the drive circuit to the probe and for supplying electrical signals indicative of the magnitude of the electrical power supplied. A manually operable input device provides a signal indicative of the transducer power level desired by the user of the probe. A control circuit is responsive to the signal indicative of the desired transducer power level and to the signals indicative of the magnitude of the supplied electrical power for providing control signals to the drive circuit to control the power applied and to control the efficiency of the application of power. The drive circuit includes an amplifier responsive to at least one of the control signals to apply power at the desired level, and also includes a regulator for supplying a supply voltage to the amplifier. The regulator is responsive to a second control signal from the control circuit to vary the peak voltage supplied by the regulator to the amplifier to substantially minimize the amplifier's power consumption.

10 Claims, 1 Drawing Sheet

PHACOEMULSIFICATION PROBE DRIVE CIRCUIT

BACKGROUND OF THE INVENTION

This invention relates to the field of phacoemulsification, and more particularly to drive circuits for phacoemulsification probes.

The use of ultrasonic handpieces or probes for the removal of cataracts in the human eye is well known. Typically, this procedure, called phacoemulsification, uses ultrasonic probes for rupturing cataracts in the eye, combined with aspiration of the resulting debris. Ultrasonic phacoemulsification probes conventionally include a piezoelectric crystal(s) affixed to a probe body. The crystal is driven by an electric power source and converts the electric power to ultrasonic power which is applied by the probe to the cataract.

The amount of power applied by the probe is a function the frequency and amplitude of the driving electrical waveform and is typically under control of the surgeon using the probe. It is known that the frequency of the applied electrical waveform should be adjusted to the resonant frequency of the probe for efficient power conversion.

Prior art drive circuits for phacoemulsification probes function adequately, but they could be improved. For example, prior art drive circuits have a level of power consumption that is higher than desirable. This high level of power consumption not only inefficient, it results in other deficiencies. Higher power consumption results in the use of larger heat sinks than would be desirable, increasing the device's total weight and size.

SUMMARY OF THE INVENTION

Among the various objects and features of the present invention may be noted the provision of a phacoemulsification probe drive circuit with improved efficiency.

A second object is the provision of such a probe drive circuit with improved power consumption.

A third object is the provision of such a probe drive circuit with reduced size and weight.

Other objects and features will be in part apparent and in part pointed out hereinafter.

Briefly, a phacoemulsification probe system of the present invention includes an ultrasonic handpiece having a distal end of a size suitable for insertion into a patient's eye for emulsifying cataracts and the like. The handpiece includes a transducer for converting electrical power to ultrasonic power for application to the patient. A drive circuit is provided for supplying electrical power to the ultrasonic handpiece transducer. Circuitry is included for sensing the electrical power supplied by the drive circuit to the ultrasonic handpiece transducer and for supplying electrical signals indicative of the magnitude of the electrical power supplied by the drive circuit. A manually operable input device is included for providing a signal indicative of the transducer power level desired by the user of the phacoemulsification probe system. A control circuit is responsive to the signal indicative of the desired transducer power level and to the signals indicative of the magnitude of the supplied electrical power for providing control signals to the drive circuit to control the power applied and to control the efficiency of the application of power. The drive circuit includes an amplifier responsive to at least one of the control signals to apply power at the desired level, and a regulator for supplying a supply voltage to the amplifier. The regulator is responsive to a second control signal from the control circuit to vary the peak voltage supplied by the regulator to the amplifier to substantially minimize the amplifier's power consumption.

A method of the present invention involves driving a phacoemulsification apparatus having an ultrasonic handpiece with a distal end of a size suitable for insertion into a patient's eye for emulsifying cataracts and the like, which handpiece includes a transducer for converting electrical power to ultrasonic power for application to the patient, which apparatus also has a drive circuit connected to the ultrasonic handpiece transducer and a manually operable input device for signaling the desired transducer power level. The method includes the steps of supplying electrical power from the drive circuit to the ultrasonic handpiece transducer, sensing the electrical power supplied by the drive circuit to the ultrasonic handpiece transducer, comparing the electrical power supplied by the drive circuit with the desired transducer power level, and using a switching regulator to vary the supply voltage to the drive circuit to efficiently supply power to the transducer. The supply voltage is varied to correspond to the desired output power selected by the manually operable input device.

BRIEF DESCRIPTION OF THE DRAWINGS

Similar reference characters indicate similar parts throughout the several views of the drawings.

DESCRIPTION OF THE PREFERRED EMBODIMENT

Turning to the drawings, a phacoemulsification probe system 11 of the present invention includes an ultrasonic handpiece or probe 13 having a distal end of a size suitable for insertion into a patient's eye for emulsifying cataracts and the like. For purposes of this invention, handpiece 13 may be of any conventional design and includes a conventional transducer for converting electrical power to ultrasonic power for application to the patient (not shown).

Figure 1:
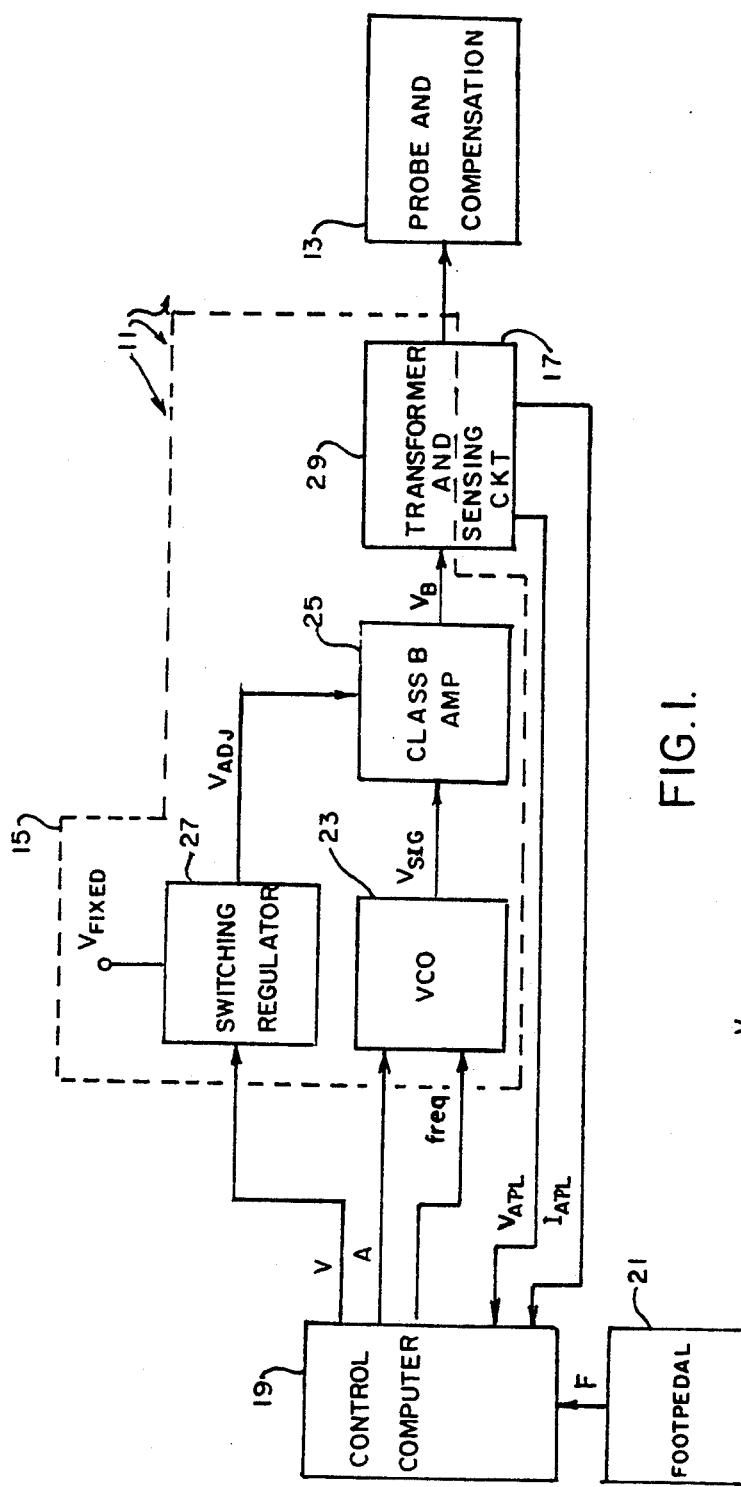
FIG. 1 is a block diagram of the phacoemulsification probe system of the present invention.

A drive circuit 15 is provided for supplying electrical power to the transducer of ultrasonic handpiece 13. The voltage (labelled VAPL on FIG. 1) and current (labelled IAPL) actually supplied by the drive circuit is sensed by conventional voltage and current sensing circuitry 17 and electrical signals representing the applied voltage VAPL and applied current IAPL are supplied from the sensing circuitry to a control computer 19. Control computer 19 may be a conventional microprocessor suitably programmed to perform the functions described herein.

In addition to inputs VAPL and IAPL, computer 19 receives an input (labelled F) from a manually operable input device 21. Input device 21 is a conventional footpedal by means of which the surgeon signals the computer to increase or decrease the output power of probe 13.

For purposes of this invention, control computer 19 has three output signals (labelled V, A, and "freq") which are provided to control drive circuit 15. It is known in the art to provide control signals A and "freq" to provide the output power at the desired level and at the resonant frequency of the probe. The present invention is not concerned with control signal "freq" which can be varied as taught in the prior art. Rather it deals with control signals A and V.

Control signals A and "freq" from the control computer are provided to a conventional voltage controlled oscillator 23 whose output is supplied to a class B amplifier 25. Power for the class B amplifier is obtained from a switching regulator 27, and the output of amplifier 25 is supplied to drive a transformer 29. The output of transformer 29 is applied to probe 13 and that same output is sensed by sensing circuit 17 as described above.

Switching regulator 27 provides a supply voltage (labelled VADJ) to amplifier 25 which is a function of the other control signal from computer 19, namely control signal V. In general control signal V is used to control the efficiency of the application of power, specifically to substantially minimize the amplifier's power consumption, while control signal A is used to control the level of power applied to the probe.

Operation of system 11 is as follows: During use of system 11 (after initial adjustment of control signal "freq" to find the resonant frequency of probe 13), control computer 19 receives signal F from footpedal 21, which signal represents the power level the user desires to be applied to probe 13. Computer 19 in response adjusts the amplitude control signal A to voltage controlled oscillator 23 to approximately supply the desired power level to the probe. The actual applied voltage and current VAPL and IAPL are sensed and signals representing them are supplied to computer 19 to close the control loop between the drive circuit and computer 19. The computer uses this information concerning the actual applied power to adjust control signal A as necessary to deliver the desired power corresponding to input signal F to the probe.

Although control of signal A results in the desired power being applied to the probe, it exerts no control over the efficiency of drive circuit 15. To control that efficiency, and thereby substantially minimize the power consumption, computer 19 further adjusts control signal V to switching regulator 27. The switching regulator (preferably a boost regulator, although other types of switching regulators could also be used) is provided with a fixed voltage (labelled VFIXED) which it regulates as commanded by control signal V. Adjustment of control signal V causes the supply voltage output VADJ of the switching regulator to change in a controlled manner.

Figure 2:
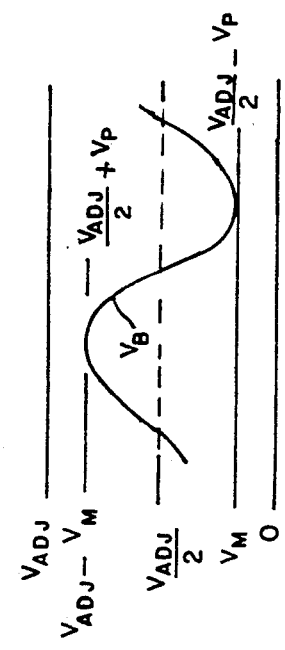
FIG. 2 is a diagram illustrating the voltage levels involved in the system of FIG. 1.

The value of supply voltage VADJ is determined as follows: Referring to FIG. 2, the voltage VB is the signal applied to transformer 29. That signal is a sine wave of amplitude VP. Thus, voltage VB has a peak to peak amplitude of 2*VP. Class B amplifier 25 works in such a way that VB=VADJ/2+VP*sinwt. Computer 19 controls switching regulator 27 so that the supply voltage VADJ remains at the level VADJ=2*VP+2*VM, as VP varies in response to footpedal signal F. VM is the marginal voltage required by the class B amplifier so that the signal is properly passed without significant distortion. If VADJ were larger than this value (2*(VP+VM)), then excess power would be dissipated in amplifier 25. If VADJ were less than this value, then the signal would be distorted.

It should be realized that although amplifier 25 is described as a class B amplifier, any number of other types of amplifiers could be used with the same invention. Numerous variations of the present constructions and methods may be used. The examples given herein are merely illustrative, and are not to be construed in a limiting sense.

What is claimed is:
1. A phacoemulsification probe system comprising:
an ultrasonic handpiece having a distal end of a size suitable for insertion into a patient's eye for emulsifying cataracts, said handpiece including a transducer for converting electrical power to ultrasonic power for application to the patient;
drive circuit means for supplying electrical power to the ultrasonic handpiece transducer;
means for sensing the electrical power supplied by the drive circuit means to the ultrasonic handpiece transducer and for supplying electrical signals indicative of the magnitude of said electrical power supplied by the drive circuit means;
manually operable input means for providing a signal indicative of a transducer power level desired by the user of the phacoemulsification probe system; and
control circuit means responsive to the signal indicative of the desired transducer power level and to the signals indicative of the magnitude of the supplied electrical power for providing control signals to the drive circuit means to control the power applied and to control the efficiency of the application of power;
said drive circuit means including amplifier means responsive to at least one of the control signals to apply power at the desired level, and regulator means for supplying a supply voltage to the amplifier means, said regulator means being responsive to a second control signal from the control circuit means to vary the magnitude of the supply voltage supplied by the regulator means to the amplifier means to substantially minimize the amplifier's power consumption.

2. The phacoemulsification probe system as set forth in claim 1 wherein the drive circuit means includes an oscillator for controlling the frequency and amplitude of the voltage supplied by the drive circuit means, said amplifier means being connected to the output of the oscillator to provide electrical power at a desired level as set by the control signals.

3. The phacoemulsification probe system as set forth in claim 2 wherein the oscillator is a shine wave oscillator, the control circuit means being responsive to the input signals to provide the control signal to the regulator means which results in the magnitude of the supply voltage from the regulator means being only slightly larger than the desired peak output voltage of the amplifier means.

4. The phacoemulsification probe system as set forth in claim 3 wherein the regulator means is controlled by the control circuit means such that the magnitude of the supply voltage equals the desired output voltage of the amplifier means plus twice a margin voltage, where the margin voltage is chosen to minimize the supply voltage while allowing the amplifier means to pass the signal from the oscillator without distortion, said control means controlling both the supply voltage and the desired output voltage of the amplifier means.

5. The phacoemulsification probe system as set forth in claim 1 wherein the regulator means is a switching regulator whose output voltage is controlled by the second control signal from the control circuit means.

6. The phacoemulsification probe system as set forth in claim 1 wherein the output of the amplifier means is connected to the input of a transformer, the output of the transformer being connected to drive the ultrasonic handpiece transducer, said means for sensing the electrical power supplied to the ultrasonic handpiece being connected to the transformer to sense said supplied electrical power.

7. A method of driving a phacoemulsification apparatus having an ultrasonic handpiece with a distal end of a size suitable for insertion into a patient's eye for emulsifying cataracts, said handpiece including a transducer for converting electrical power to ultrasonic power for application to the patient, said apparatus also having a drive circuit connected to the ultrasonic handpiece transducer and also having a manually operable input device for signaling a desired transducer power level, said method comprising:

supplying electrical power from the drive circuit to the ultrasonic handpiece transducer;

sensing the electrical power supplied by the drive circuit to the ultrasonic handpiece transducer;

comparing the electrical power supplied by the drive circuit with the desired transducer power level; and using a switching regulator to vary the magnitude of a supply voltage to the drive circuit to efficiently supply power to the transducer, said magnitude of the supply voltage being varied to correspond to the desired output power selected by the manually operable input device.

8. The method as set forth in claim 7 wherein the drive circuit includes an oscillator for controlling the frequency and amplitude of the voltage supplied by the drive circuit and an amplifier connected to the output of the oscillator, said amplifier being connected to the supply voltage and having a desired output voltage corresponding to the desired transducer power level, the magnitude of the supply voltage from the switching regulator being chosen to be slightly greater than the desired output voltage from the amplifier so that the power consumption of the drive circuit is minimized.

9. The method as set forth in claim 8 wherein the switching regulator is controlled to provide a supply voltage equal to the desired output voltage of the amplifier plus twice a margin voltage, where the margin voltage is chosen to minimize the supply voltage while allowing the amplifier to pass the signal from the oscillator without distortion so that both the supply voltage and the desired output voltage of the amplifier are controlled.

10. The method as set forth in claim 8 wherein the oscillator is a sine wave oscillator, further including the step of controlling the magnitude of the supply voltage to a level which is only slightly larger than the desired peak output voltage of the amplifier in order to minimize the power dissipated in the amplifier.

* * * * *